United States Patent [19]

Coy et al.

[11] 4,127,540

[45] Nov. 28, 1978

[54] NOVEL DERIVATIVES OF δ-ENDORPHINS, INTERMEDIATES THEREFOR, AND COMPOSITIONS AND METHODS EMPLOYING SAID DERIVATIVES

[76] Inventors: David H. Coy, 4319 Perrier St., New Orleans, La. 70115; Abba J. Kastin, 4400 Morales St., New Orleans, La. 70002

[21] Appl. No.: 807,215

[22] Filed: Jun. 16, 1977

[51] Int. Cl.² .................... C08L 37/00; C07C 103/52; A61K 37/00
[52] U.S. Cl. ................................ 260/8; 260/112.5 R; 424/177
[58] Field of Search ................ 260/112.5 R, 112.5 E, 260/8; 424/177

[56] References Cited

U.S. PATENT DOCUMENTS 4,038,222  7/1977  Li ........................................ 424/177

OTHER PUBLICATIONS

Cox et al., Proc. Natl. Acad. Sci. USA 73, 1976 pp. 1821–1823.
Lazarus et al., Proc. Natl. Acad. Sci. USA 73, 1976 pp. 2156–2159.
Ling et al., Chem. Abst. 86, 1977 p. 38887H.
Ling et al., Proc. Natl. Acad. Sci. USA 73, 1976 pp. 3308–3310.
Guillemin, et al. Biochimie 1976 pp. 783–785.
Bradbury et al., Nature 260, 1976 pp.793–795.
Li et al., Proc. Natl. Acad. Sci. USA 73, 1976 pp. 1145–1148.
Coy et al., Biochem and Biophys. Res. Comm. 73, 1976 pp. 632–638.
Pert., et al., Opintes and Endogenous Oipioid Peptides, 1976 pp. 79–86.
Plotnikoff et al., Life Science 19, pp. 1283–1288 1976.
Kosterlitz et al., Life Science 17, pp. 91–96, 1975.
Pert et al., Science 194, pp. 330–332, 1976.
Ling et al., Biochem. and Biophys. Res. Comm. 74, 1977 pp. 248–255.
Marks et al., Biochem. and Biophys. Res. Comm. 74, 1977 pp. 1552–1559.

*Primary Examiner*—Delbert R. Phillips
*Attorney, Agent, or Firm*—Joyce R. Niblack

[57] ABSTRACT

Novel δ-endorphins represented by the formula:

H-Tyr-X-Gly-Phe-Met-Thr-Ser-Glu-Lys-Ser-Gln-
Thr-Pro-Leu-Val-Thr-Leu-Phe-Lys-Asn-Ala-Ile-
Ile-Lys-Asn-Ala-Tyr-Y                              I.

wherein: X is a chiral residue of a D-amino acid selected from the group consisting of D-alanine, D-leucine, D-isoleucine, D-valine, D-phenylalanine, D-tyrosine, D-tryptophan, D-serine, D-threonine, D-methionine, D-glutamic acid, D-glutamine, D-proline D-aspartic acid, D-asparagine, D-lysine, D-arginine and D-histidine; and Y is selected from the group consisting of hydroxy, amino, loweralkylamino, diloweralkylamino and lower alkoxy; and the pharmaceutically acceptable salts thereof; intermediates useful in making the novel compounds; and pharmaceutical compositions and methods employing the novel compounds.

20 Claims, No Drawings

NOVEL DERIVATIVES OF δ-ENDORPHINS, INTERMEDIATES THEREFOR, AND COMPOSITIONS AND METHODS EMPLOYING SAID DERIVATIVES

BACKGROUND OF THE INVENTION

While there are a number of analgesic agents currently utilized to relieve mild to severe pain, the search for improved analgesics is a continuing one because of the numerous problems associated with the presently available agents. Aspirin and related salicylates are considered to be non-narcotic analgesic agents useful for relieving mild to moderate pain in addition to their usefulness as anti-inflammatory and anti-pyretic agents. However, the ingestion of salicylic acid or related salicylates may result in epigastric distress, nausea and vomiting. This widely used class of non-narcotic analgesic agents may also cause gastric ulceration and even hemorrhage both in experimental animals and man. Exacerbation of peptic ulcer symptoms and erosive gastritis have all been reported in patients on high dose therapy, i.e., arthritis patients. Aspirin is also one of the most common causes of drug poisoning in young children and has a potential of serious toxicity if used improperly.

Acetaminophen is also considered to be a non-narcotic analgesic agent useful in treating mild pain associated with simple headache, common muscular aches, etc. While acetaminophen is particularly useful for patients who cannot take aspirin, i.e., ulcer patients, its use is contraindicated in individuals who have exhibited a sensitivity to it. In addition to their drawbacks in view of their potential side effects, the mild non-narcotic analgesic agents are not sufficiently potent to relieve the severe pain associated with surgery, cancer and the like.

Unfortunately, the potent analgesic agents capable of relieving such severe pain are also narcotic agents and their use entails the risk of producing physical and sometimes psychological dependence. There are as yet no agents effective against severe pain that are entirely free of this risk.

Thus, there is an urgent need for improved analgesic agents for treating mild as well as severe pain. The present invention provides such agents.

In addition to the need for improved analgesic agents, there is also a need for improved psychotropic agents to replace or to provide an alternative to current therapy. The compounds of this invention, in addition to their analgesic activity, also exhibit anti-depressant, tranquilizing, and sedative-hypnotic activity. Thus, their usefulness as analgesic agents is enhanced since many patients suffering from pain also exhibit varying states of anxiety and depression.

A recently identified pentapeptide, methionine enkephalin, has the following structure: H-Tyr-Gly-Gly-Phe-Met-OH [see Hughes et al., *Nature*, 258, 577 (1975)]. This peptide is found in many areas of the brain where it appears to act as a neurotransmitter or neuromodulator in a central pain suppressive system. The natural peptide binds stereospecifically to partially purified brain opiate receptor sites [for instance see Bradbury et al., *Nature*, 260, 793 (1976)] is very active in bioassays for opiate activity, but exhibits only weak analgesic agent of short duration when injected directly into the brain of the rat, [for instance, see Belluzzi et al., *Nature*, 260, 625 (1976)].

In addition, several C-terminal fragments of a 91 chain length brain peptide, β-lipotropin having the pentapeptide sequence of methionine enkephalin at their N-terminus have been isolated from the brain and found to exhibit potent opioid activity in binding to partially purified brain opiate receptor sites. See Ling and Guillemin, *Proc. Natl. Acad. Sci. USA* 73, 3308 (1976) and *Proc. Natl. Acad. Sci. USA* 73, 1821 (1976). The reported fragments have been characterized as α-endorphin (61–76), β-endorphin (61–91), γ-endorphin (61–77) and δ-endorphin (61–87) [β-LPH] 61–64 β-LPH]-61–68 [β-LPH] 61–69 and [β-LPH]61–79. Unlike the natural enkephalins, the parent endorphins exhibit some degree of analgesic activity; but only when administered intracerebrally or parenterally. However, the compounds of this invention, derivatives of δ-endorphin, are highly active by parentereal as well as other routes of administration.

We have unexpectedly found that the incorporation of a D-amino acid, such as D-alanine, for the penultimate glycine residue at the end terminus of δ-endorphin greatly enhances the analgesic activity of these compounds. In addition to their analgesic activity, the compounds of the present invention also exhibit excellent anti-depressant, sedative-hypnotic, and tranquilizing activity.

SUMMARY OF THE INVENTION

This invention relates to novel heptacosapeptides and more specifically relates to novel δ-endorphin derivatives of human β-liptropin fragment 61–87. The compounds of this invention are δ-endorphins substituted in the 2-position by a D-amino acid and the corresponding amides and alkylamide, dialkylamides, esters and their salts. The peptides of this invention are useful as analgesic, tranquilizer, sedative, hypnotic, prolactin releasing and growth hormone releasing antidepressant agents, and pharmaceutical compositions and methods employing such novel heptacosapeptides are also disclosed herein. Intermediates useful in the synthesis of the novel δ-endorphin derivatives are also included within the scope of this invention.

DETAILED DESCRIPTION OF PREFERRED EMBODIMENTS

The heptacosapeptides of this invention have the following amino acid sequence set forth in formula I:

H-Tyr-X-Gly-Phe-Met-Thr-Ser-Glu-Lys-Ser-Gln-
Thr-Pro-Leu-Val-Thr-Leu-Phe-Lys-Asn-Ala-Ile-
Ile-Lys-Asn-Ala-Tyr-Y        (I)

wherein X is a D-amino acid selected from the group consisting of D-alanine, D-leucine, D-isoleucine, D-valine, D-phenylalanine, D-tyrosine, D-tryptophan, D-serine, D-threonine, D-histidine, D-methionine, D-glutamic acid, D-glutamine, D-aspartic acid, D-asparagine, D-lysine D-arginine; and Y is selected from the group consisting of hydroxy, amino, aminoloweralkyl, aminodiloweralkyl or loweralkoxy and the pharmaceutically acceptable salts thereof.

All chiral amino acid residues identified herein are in the natural or L-configuration unless otherwise specified.

In keeping with standard peptide nomenclature, abbreviations for chiral amino acid residues are used herein as follows:

| | | | |
|---|---|---|---|
| Tyr | - L-tyrosine | Ile | - L-isoleucine |
| D-Tyr | - D-tyrosine | D-Ile | - D-isoleucine |
| Gly | - glycine | Leu | - L-leucine |
| Phe | - L-phenylalanine | D-Leu | - D-leucine |
| D-Phe | - D-phenylalanine | Thr | - L-threonine |
| Met | - L-methionine | D-Thr | - D-threonine |
| D-Met | - D-methionine | Val | - L-valine |
| Ala | - L-alanine | D-Val | - D-valine |
| D-Ala | - D-alanine | Pro | - L-proline |
| Ser | - L-serine | D-Pro | - D-proline |
| D-Ser | - D-serine | Gln | - L-glutamine |
| Lys | - L-lysine | D-Gln | - D-glutamine |
| D-Lys | - D-lysine | Glu | - L-glutamic acid |
| Asn | - L-asparagine | D-Glu | - D-glutamic acid |
| D-Asn | - D-asparagine | Trp | - L-tryptophan |
| His | - L-histidine | D-Trp | - D-tryptophan |
| D-His | - D-histidine | D-Asp | - D-aspartic acid |

The term "pharmaceutically acceptable salts," as used herein, refers to the non-toxic alkali metal, alkaline earth metal and ammonium salts commonly used in the pharmaceutical industry including the sodium, potassium, lithium, calcium, magnesium, barium and ammonium salts which are prepared by methods well known in the art. The term also includes non-toxic acid addition salts which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

The term "lower alkyl" refers to straight and branched chain alkyl groups having from 1 to 6 carbon atoms such as methyl, ethyl, n-propyl, iso-propyl, n-butyl, iso-butyl, tert-butyl, n-pentyl, 2-pentyl, n-hexyl, and the like.

The term lower alkoxy refers to alkoxy groups having from 1 to 6 straight or branced chain carbon atoms, i.e., methoxy, ethoxy, n-propoxy and the like.

Also contemplated within the scope of the present invention are the following intermediates of formula II which are useful in preparing the heptacosanapeptides of Formula I:

R$_1$-Tyr(R$_2$)-X-Gly-Phe-Met-Thr(R$_3$)-Ser(R$_3$)-Glu(R$_4$)-Lys(R$_5$)-Ser(R$_3$)-Gln-Thr(R$_3$)-Pro-Leu-Val-Thr(R$_3$)-Leu-Phe-Lys(R$_5$)-Asn-Ala-Ile-Ile-Lys(R$_5$)-Asn-Ala-Tyr(R$_2$)-Y    (II)

wherein

X' is equal to X as defined in Formula I above, except in the case of D-threonine, D-serine, D-tyrosine, D-glutamic acid, D-arginine, D-asparagine and D-lysine, in which cases x is a chiral residue of a D-amino acid as defined in Formula I protected by an R$_2$, R$_3$, R$_4$, R$_5$ or R$_6$ protecting group as defined below;

R$_1$ is a solid state peptide synthesis N-terminus protecting group. or 2-bromobenzyloxycarbonyl (2-BrZ);

R$_3$ is a protecting group for the alcohol hydroxy functions of serine and threonine, selected from the group defined above for R$_2$;

R$_4$ is a protecting group for the gamma carboxyl group of glutamic acid selected from the group consisting of tert-butyl, benzyl, and 4-chlorobenzyl;

R$_5$ is a protecting group for the epsilon amino group of lysine selected from the group consisting of trifluoroacetyl, benzyloxycarbonyl or, preferably, 2-chlorobenzyloxycarbonyl; and R$_6$ is a protecting group for the guanidine group of arginine and is selected from the group of nitro or tosyl.

Y is as defined in Formula I above or a derivatized insoluble polystyrene resin support represented by Formulae III or IV:

   (III)

   (IV)

The term "acyl-type protecting groups" refers to groups illustrated by but not restricted to formyl, trifluoroacetyl, tosyl, nitrosulfonyl, and the like.

The term "aromatic urethan-type protecting groups" is represented by groups such as benzyloxycarbonyl, p-methoxybenzyloxycarbonyl, p-biphenylisopropyloxycarbonyl, 2,5-dimethoxyphenylisopropyloxycarbonyl, and the like.

The term "cycloalkyl urethan protecting group," as used herein, refers to groups such as cyclopentyloxycarbonyl, adamantyloxycarbonyl, cyclohexyloxycarbonyl, isobornyloxycarbonyl, etc.

The term "acyl type protecting groups" refers to groups illustrated by but not restricted to the following such as formyl, trifluoroacetyl, tosyl, nitrosulfenyl, and the like.

The term "aromatic urethan-type protecting groups" is represented by groups such as benzyloxycarbonyl, p-methoxybenzyloxycarbonyl, p-biphenyl, isopropyloxycarbonyl, 2,5-dimethoxyphenyl isopropyloxycarbonyl, and the like.

The term "cycloalkyl urethan protecting groups", as used herein, refers to groups such as cyclopentyloxycarbonyl, adamantyloxycarbonyl, cyclohexylcarbonyl, isobornyloxycarbonyl, etc.

"Urethan type protecting groups" include but are not limited to groups such as phenylthiocarbonyl.

"Alkyl type protecting groups" are those commonly used in the art such as trityl.

"Trialkylsilane groups" include compounds such as trimethylsilane, triethylsilane, tributylsilane, and the like.

The preferred protecting groups, the "aliphatic urethan protecting groups", include tert-butyloxycarbonyl, diisopropyloxycarbonyl, isopropyloxycarbonyl, allyloxycarbonyl and the like.

The polystyrene resin support is preferably a copolymer of styrene with 1–2% divinylbenzene as a crosslinking agent which causes the polystyrene polymer to be completely insoluble in most organic solvents. In formula II, $\phi$ is phenyl.

In selecting a particular side-chain protecting group to be used in the synthesis of the peptides, several conditions must be met: (a) the protecting group must be stable to the reagent and under reaction conditions selected for removing the α-amino protecting group at each step of the synthesis; (b) the protecting group must retain its protecting properties and not be chemically modified; and (c) the side-chain protecting group must be removable at the end of the solid-phase synthesis under reaction conditions that will not alter the peptide chain.

The peptides are prepared using standard solid-phase techniques. The synthesis is commenced from the C-terminal end of the peptide using an α-amino protected resin. A suitable starting material can be prepared, for instance, by attaching the required α-amino acid to a chloromethylated resin, a hydroxymethyl resin, or a benzhydrylamine resin. One such chloromethylated resin is sold under the trade name Bio-beads SX-1 by Bio Rad Laboratories, Richmond, California and the prepreparation of the hydroxymethyl resin is described by Bodonszky et al., *Chem. Ind.* (London) 38, 1597 (1966). The benzhydrylamine resin has been described by Pietta and Marshall, *Chem. Commun.*, 650 (1970) and is commercially available from Beckman Instrument, Palo Alto, California.

In the preparation of the compounds of this invention an α-amino protected amino acid is coupled to the chloromethylated resin with the aid of, for example, cesium bicarbonate catalyst, according to the method described by Gisin, *Helv, Chim. Acta,* 56, 1476 (1973). After the initial coupling, the α-amino protecting group is removed by a choice of reagents including trifluoroacetic acid or hydrochloric acid solutions in organic solvents at room temperature. After removal of the α-amino protecting group, the remaining protected amino acids are coupled stepwise in the desired order to obtain the compounds of Formula II. Each protected amino acid is generally reacted in a 3-fold excess using an appropriate carboxyl group activator such as dicyclohexylcarbodiimide in solution in, for example, methylene chloride-dimethylformamide mixtures.

After the desired amino acid sequence has been completed, the desired peptide is removed from the resin support by treatment with a reagent such as hydrogen fluoride which not only cleaves the peptide from the resin, but also cleaves all remaining side-chain protecting groups. When the chloromethylated resin is used, hydrogen fluoride treatment results in the formation of the free peptide acids of Formula I (Y=OH). When the benzhydrylamine resin is used, hydrogen fluoride treatment results directly in the free peptide amides of Formula I (Y=NH$_2$). Alternatively, when the chloromethylated resin is employed, the side-chain protected peptide can be cleaved by treatment of the peptide-resin with ammonia to give the desired side-chain protected amide or with an alkylamine to give a side-chain protected alkylamide. Side-chain protection is then removed in the usual fashion by treatment with hydrogen fluoride to give the free amides or alkylamides.

The solid-phase procedure discussed above is well known in the art and has been essentially described by J. M. Stewart, "Solid Phase Peptide Synthesis" (Freeman and Co., San Francisco, 1969).

The compounds of formula I are useful as analgesic, and anti-depressant, tranquilizing and sedative agents when administered to mammalian hosts at dosages of from 0.001 to 100 mg/kg of body weight daily, preferably in divided dosages. The compounds are preferably administered by parenteral routes, i.e., the intravenous, intraperitoneal, intramuscular or subcutaneous, routes of administration. The compounds may also be administered by a variety of other routes including oral or sublingual or by vaginal, rectal or nasal routes of administration. Accordingly, one aspect of the present invention includes pharmaceutical compositions suitable for such routes of administration.

The analgesic activity of the compounds of Formula I was established in the rat tail flick test as described by D'Amour and Smith, *J. Pharmac. Exp. Ther.,* 72, 74 (1941). The presently preferred analgesic agent of this invention is D-Ala$^2$-human-δ-lipotropin fragment (61–87) (also known as D-Ala$^2$-δ-endorphin).

For the purpose of this invention, the terms endorphin and lipotropin shall be used to refer to human endorphins or lipotropin fragments.

The anti-depressant (stimulant) activity and the tranquilizing and sedative-hypnotic activity of the compounds of Formula I were first established in the open field test described by Kulkarni et al. *Pharmakopsychiatrie Neuro-Psychopharamkologie* 8(1): pp 45–50 (1975) and the self stimulation test described by Bailey et al., *Research Communications in Chemical Pathology and Pharmacology* 11(4): pp. 543–552 (1975).

The dosage administered depends upon the desired effect. For example, the degree of analgesia produced by the compounds of this invention may be varied by varying the dosage. Anti-depressant activity is observed at the lower dosages, i.e., 0.001 to 5 mg/kg and sedation or tranquilization is produced by dosages of greater than 5 mg/kg of body weight.

The following compounds are illustrative of the peptacosapeptides of Formula I. Compounds of Formula I will hereinafter be designated as derivatives of α-endorphin. The D-amino acid is designated as being in the 2-position. Compounds wherein Y- is OH are named as substituted δ-endorphins and are illustrated by the following:

D-Ala$^2$-δ-endorphin;
D-Leu$^2$-δ-endorphin;
D-Ile$^2$-δ-endorphin;
D-Val$^2$-δ-endorphin;
D-Phe$^2$-δ-endorphin;
D-Tyr$^2$-δ-endorphin;
D-Try$^2$-δ-endorphin;
D-Ser$^2$-δ-endorphin, sodium salt;
D-Thr$^2$-δ-endorphin;
D-Met$^2$-δ-endorphin; calcium salt;
D-Glu$^2$-δ-endorphin;
D-His$^2$-δ-endorphin;
D-Gln$^2$-δ-endorphin; ammonium salt;
D-Asp$^2$-δ-endorphin;
D-Asn$^2$-δ-endorphin;
D-Lys$^2$-δ-endorphin;
D-Arg$^2$-δ-endorphin;

The endorphin amides of this invention include but are not limited to the following:

D-Ala$^2$-δendorphin amide;
D-Leu$^2$-δendorphin amide;
D-Ile$^2$-δendorphin amide;
D-Val$^2$-δendorphin amide;
D-Phe$^2$-δendorphin amide;
D-Tyr$^2$-δendorphin amide;
D-Trp$^2$-δendorphin amide;
D-Ser$^2$-δendorphin amide;
D-Thr$^2$-δendorphin amide;
D-Met$^2$-δendorphin amide;
D-Glu$^2$-δ-endorphin amide;
D-Gln$^2$-δ-endorphin amide;
D-Asp$^2$-δ-endorphin amide;
D-Asn$^2$-δ-endorphin amide;
D-Lys$^2$-δ-endorphin amide;
D-Arg$^2$-δ-endorphin amide;
D-Ala$^2$-δ-endorphin amide hydrochloride;
D-Leu$^2$-δ-endorphin amide citrate;

D-Ile$^2$-δ-endorphin amide hydrobromide;
D-Val$^2$-δ-endorphin amide hydroiodide;
D-Phe$^2$-δ-endorphin amide hydrochloride;
D-Tyr$^2$-δ-endorphin amide sulfate;
D-Trp$^2$-δ-endorphin amide lactate;
D-Ser$^2$-δ-endorphin amide napsylate;
D-Thr$^2$-δ-endorphin amide oleate;
D-Met$^2$-δ-endorphin amide valerate;
D-Glu$^2$-δ-endorphin amide tosylate;
D-Gln$^2$-δ-endorphin amide disulfate;
D-Asp$^2$-δ-endorphin amide benzoate;
D-Asn$^2$-δ-endorphin amide acetate;
D-Lys$^2$-δ-endorphin amide laurate;
D-Arg$^2$-δ-endorphin amide phosphate;
D-Ala$^2$-δ-endorphin methylamide;
D-Leu$^2$-δ-endorphin ethylamide;
D-Ile$^2$-δ-endorphin n-propylamide;
D-Val$^2$-δ-endorphin n-butylamide;
D-Phe$^2$-δ-endorphin tert-butylamide;
D-Tyr$^2$-δ-endorphin sec-butylamide;
D-Trp$^2$-δ-endorphin n-pentylamide;
D-Ser$^2$-δ-endorphin ethylamide;
D-Thr$^2$-δ-endorphin dimethylamide;
D-Met$^2$-δ-endorphin diethylamide;
D-Glu$^2$-δ-endorphin n-propylamide;
D-Gln$^2$-δ-endorphin-iso-propylamide; and the like.

Esters of this invention include but are not limited to the following:
D-Ala$^2$-δ-endorphin, methyl ester;
D-Val$^2$-δ-endorphin, ethyl ester;
D-Met$^2$-δ-endorphin, n-propyl ester;
D-Phe$^2$-δ-endorphin, iso-propyl ester;
D-Glu$^2$-δ-endorphin, n-butyl ester;
D-Gln$^2$-δ-endorphin, n-pentyl ester;
D-Ser$^2$-δ-endorphin, n-hexyl ester; and the like.

The following examples further illustrate the present invention:

The following examples further illustrate the present invention:

EXAMPLE 1

Preparation of O-2-bromobenzyloxycarbonyl-L-tyrosyl-D-alanyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-L-leucyl-L-phenylalanyl-N-epsilon-2-chlorobenzyloxycarbonyl-L-lysyl-L-asparaginyl-L-alanyl-L-isoleucyl-L-isoleucyl-N-epsilon-2-chlorobenzyloxycarbonyl-L-lysyl-L-asparaginyl-L-alanyl-O-2-bromobenzyloxycarbonyl-L-tyrosyl-O-CH$_2$-resin. (D-Ala$^2$-δ-endorphin or D-Ala$^2$-β lipotropin fragment 61-87 protected resin).

Tert-butyloxycarboxyl-O-2-bromobenzyloxycarbonyl-L-tyrosine-O-CH$_2$-resin (1.0 mmole), prepared by the method of Gisin, *Helv. Chim. Acta*, 56, 1476 (1973), is placed in the reaction vessel of a Beckman Model 990 automatic peptide synthesizer programmed to carry out the following cycle of washes and reactions: (a) methylene chloride; (b) 25% trifluoroacetic acid in methylene chloride (2 times for 1.5 and 15 minutes each); (c) 50% trifluoroacetic acid in methylene chloride (1t minutes); (d) methylene chloride; (e) ethanol; (f) methylene chloride; (g) 10% triethylamine in methylene chloride (2 times for 5 minutes each); and (h) methylene chloride.

The deprotected resin is then stirred with tert-butyloxycarbonyl (t-Boc) alanine (3.0 mmoles) in methylene chloride and dicyclohexylcarbodiimide (3.0 mmoles) is added thereto. The mixture is stirred at room temperature for 2 hours and the peptide resin is then washed successively with methylene chloride ethanol and methylene chloride. Two percent N-acetyl-imidazole in methylene chloride is then added and the mixture stirred for 15 minutes in order to irreversibly acetylate unreacted free amino groups. The resin is then washed with methylene chloride followed by ethanol and then steps (a) through (h) are repeated as described above.

The remaining 25 Boc-amino acids are then coupled successively by the same cycle of events and the completed peptide-resin is washed with methanol (3 times) and dried under reduced pressure whereupon the desired material is obtained.

EXAMPLE 2

Preparation of L-tyrosyl-D-alanyl-glycyl-L-phenylalanyl-L-methionyl-L-threonyl-L-seryl-L-glutamyl-L-lysyl-L-seryl-L-glutamyl-L-threonyl-L-prolyl-L-leucyl-L-valyl-L-threonyl-L-leucyl-L-phenylalanyl-L-lysyl-L-asparaginyl-L-alanyl-L-isoleucyl-L-isoleucyl-L-lysyl-L-asparaginyl-L-alanyl-L-tyrosinel (D-Ala$^2$-β-endorphin) D-Ala$^2$-β-lipotropin fragment 61-87).

Removal of the protecting groups and cleavage of the peptide from the resin obtained according to the method of Example 1 is carried out by treating 0.5 mmole of the peptide-resin with hydrogen fluoride (40 ml) and anisole (4 ml) at 0° for 45 minutes. The hydrogen fluoride is then removed under reduced pressure and the anisole is removed by washing with ethyl acetate.

The crude peptide is purified by gel filtration on a column (2.5 × 95 cm) of Sephadex G50 gel by elution with 2 molar acetic acid and fractions shown to contain a major peak by uv absorption at 280 nm are pooled and evaporated to dryness. The residual oil is applied to a column (2.5 × 95 cm) of Sephadex G50 gel previously equilibrated with the lower phase followed by the upper phase of a 0.1% acetic acid: n-butanol: pyridine (11:5:3) solvent system. Elution with the upper phase yields a major symmetrical peak, determined by Folin-Lowry measurements, and material from this area is evaporated to dryness and lyophilized from water. The resulting powder is eluted on a column (1.5 × 45 cm) of carboxymethylcellulose with a linear gradient of ammonium acetate buffer (0.1 M, pH 4.6 to 0.4 M, pH 7.0) and the major symmetrical peak, as determined by uv absorption, yields the desired product as a powder after repeated lyophilization.

EXAMPLE 3

D-Leu$^2$-protected β-lipotropin fragment 61-87 —O—CH$_2$ resin is prepared by the method of Example 1, using t-Boc D-leucine in place of t-Boc D-alanine.

EXAMPLE 4

D-Leu$^2$-β-lipotropin fragment 61-87 is prepared from the protected peptide resin of Example 3 by the method of Example 2.

EXAMPLE 5

D-Ile$^2$-protected β-lipotropin fragment 61-87 —O—CH$_2$ resin is prepared by the method of Example 1, using t-Boc D-isoleucine in place of t-Boc D-alanine.

EXAMPLE 6

D-Ile$^2$-β-lipotropin fragment 61–87 is prepared from the protected peptide resin of example 5 by the method of Example 2.

EXAMPLE 7

D-Val$^2$-protected β-lipotropin fragment 61–87 —O—CH$_2$ resin is prepared by the method of Example 1, using t-Boc D-valine in place of t-Boc D-alanine.

EXAMPLE 8

D-Val$^2$-β-lipotropin fragment 61–87 is prepared from the protected peptide resin of Example 7 by the method of Example 2.

EXAMPLE 9

D-Phe$^2$-protected β-lipotropin fragment 61–87 —O—CH$_2$ resin is prepared by the method of Example 1, using t-Boc D-phenylalanine in place of t-Boc D-alanine.

EXAMPLE 10

D-Phe$^2$-β-lipotropin fragment 61–87 is prepared from the protected peptide resin of Example 9 by the method of Example 2.

EXAMPLE 11

O-2-Bromobenzyloxycarbonyl-D-Tyr$^2$-protected β-lipotropin fragment 61–87 —O—CH$_2$ resin is prepared by the method of Example 1, using t-boc O-2-bromobenzyloxycarbonyl-D-tyrosine in place of t-Boc D-alanine.

EXAMPLE 12

D-Tyr$^2$-β-lipotropin fragment 61–87 is prepared from the protected peptide resin of Example 11 by the method of Example 2.

EXAMPLE 13

D-Trp$^2$-protected β-lipotropin fragment 61–87 —O—CH$_2$ resin is prepared by the method of Example 1, using t-Boc D-tryptophan in place of t-Boc D-alanine.

EXAMPLE 14

D-Trp$^2$-β-lipotropin fragment 61–87 is prepared from the protected peptide resin of Example 13 by the method of Example 2.

EXAMPLE 15

O-Benzyl-D-Ser$^2$-protected β-lipotropin fragment 61–87 —O—CH$_2$ resin is prepared by the method of Example 1, using t-boc-O-benzyl-D-serine in place of t-Boc D-alanine.

EXAMPLE 16

D-Ser$^2$-β-lipotropin fragment 61–87 is prepared from the protected peptide resin of Example 15 by the method of Example 2.

EXAMPLE 17

O-Benzyl-D-Thr$^2$-protected β-lipotropin fragment 61–87 —O—CH$_2$ resin is prepared by the method of Example 1, using t-boc-O-benzyl-D-threonine in place of t-Boc D-alanine.

EXAMPLE 18

D-Thr$^2$-β-lipotropin fragment 61–87 is prepared from the protected peptide resin of Example 17 by the method of Example 2.

EXAMPLE 19

D-Met$^2$-protected β-lipotropin fragment 61–87 —O—CH$_2$ resin is prepared by the method of Example 1, using t-Boc D-methionine in place of t-Boc D-alanine.

EXAMPLE 20

D-Met$^2$-β-lipotropin fragment 61–87 is prepared from the protected peptide resin of Example 19 by the method of Example 2.

EXAMPLE 21

Gamma-benzyl-D-Glu$^2$-protected β-lipotropin fragment 61–87 —O—CH$_2$ resin is prepared by the method of Example 1, using t-Boc gamma-benzyl-D-glutamic acid in place of t-Boc D-alanine.

EXAMPLE 22

D-Glu$^2$-β-lipotropin fragment 61–87 is prepared from the protected peptide resin of Example 21 by the method of Example 2.

EXAMPLE 23

Gln$^2$-protected β-lipotropin fragment 61–87 —O—CH$_2$ resin is prepared by the method of Example 1, using t-Boc D-glutamine in place of t-Boc D-alanine.

EXAMPLE 24

Gln$^2$-β-lipotropin fragment 61–87 is prepared from the protected peptide resin of Example 23 by the method of Example 2.

EXAMPLE 25

α-Benzyl-D-Asp$^2$-protected β-lipotropin fragment 61–87 O—CH$_2$ resin is prepared by the method of Example 1, using t-Boc-α-benzyl-D-aspartic acid in place of t-Boc D-alanine.

EXAMPLE 26

D-Asp$^2$-β-lipotropin fragment 61–87 is prepared from the protected peptide resin of Example 25 by the method of Example 2.

EXAMPLE 27

D-Asn$^2$-protected β-lipotropin fragment 61–87 —O—CH$_2$ resin is prepared by the method of Example 1, using t-Boc D-asparagine in place of t-Boc D-alanine.

EXAMPLE 28

D-Asn$^2$-β-lipotropin fragment 61–87 is prepared from the protected peptide resin of Example 27 by the method of Example 2.

EXAMPLE 29

N-epsilon-2-chlorobenzyloxycarbonyl-D-Lys$^2$-protected β-lipotropin fragment 61–87 —O—CH$_2$ resin is prepared by the method of Example 1, using t-Boc-N-epsilon-2-chlorobenzyloxycarbonyl-D-lysine in place of t-Boc D-alanine.

EXAMPLE 30

D-Lys$^2$-β-lipotropin fragment 61–87 is prepared from the protected peptide resin of Example 29 by the method of Example 2.

EXAMPLE 31

N-guanidinotosyl-D-Arg$^2$-protected β-lipotropin fragment 61–87 —O—CH$_2$ resin is prepared by the method of Example 1, using t-Boc-N-guanidinotosyl-D-arginine$^2$ in place of t-Boc D-alanine.

EXAMPLE 32

D-Arg$^2$-β-lipotropin fragment 61–87 is prepared from the protected peptide resin of Example 31 by the method of Example 2.

EXAMPLE 33

D-Ala$^2$-protected β-lipotropin fragment 61–87 benzhydrylamine resin is prepared using the conditions described in Example 1, by successively coupling the t-Boc derivative of each amino acid to benzhydrylamine resin, purchased from Beckman Instruments, Palo Alto, Calif., instead of the O—CH$_2$ resin employed in Example 1.

EXAMPLE 34

D-Ala$^2$-β-lipotropin fragment 61–87 amide is prepared from the protected peptide resin of Example 33 by the method of Example 2.

EXAMPLE 35

D-Leu$^2$-protected β-lipotropin fragment 61–87 benzhydrylamine resin is prepared by the method of Example 33 using t-Boc D-leucine in place of t-Boc D-alanine.

EXAMPLE 36

D-Leu$^2$-β-lipotropin fragment 61–87 amide is prepared from the protected peptide resin of Example 35 by the method of Example 2.

EXAMPLE 37

D-Ile$^2$-protected β-lipotropin fragment 61–87 benzhydrylamine resin is prepared by the method of Example 33, using t-Boc-D-isoleucine in place of t-Boc-D-alanine.

EXAMPLE 38

D-Ile$^2$-β-lipotropin fragment 61–87 amide is prepared from the resin of Example 37 by the method of Example 2.

EXAMPLE 39

D-Val$^2$-protected β-lipotropin fragment 61–87 benzhydrylamine resin is prepared by the method of Example 33, using t-Boc-D-valine in place of t-Boc-D-alanine.

EXAMPLE 40

D-Val$^2$-β-lipotropin fragment 61–87 amide is prepared from the protected peptide resin of Example 39 by the method of Example 2.

EXAMPLE 41

D-Phe$^2$-protected β-lipotropin fragment 61–87 benzhydrylamine resin is prepared by the method of Example 33, using t-Boc-D-phenylalanine in place of t-Boc-D-alanine.

EXAMPLE 42

D-Phe$^2$-β-lipotropin fragment 61–87 amide is prepared from the protected peptide resin of Example 41 by the method of Example 2.

EXAMPLE 43

2-Bromobenzyloxycarbonyl-D-Tyr$^2$-protected β-lipotropin fragment 61–87 benzhydrylamine resin is prepared by the method of Example 33, using t-Boc-2-bromobenzyloxycarbonyl-D-tyrosine in place of t-Boc D-alanine.

EXAMPLE 44

D-Tyr$^2$-β-lipotropin fragment 61–87 amide is prepared from the protected peptide resin of Example 43 by the method of Example 2.

EXAMPLE 45

D-Trp$^2$-protected β-lipotropin fragment 61–87 benzhydrylamine resin is prepared by the method of Example 33 using t-Boc D-tryptophan in place of t-Boc D-alanine.

EXAMPLE 46

D-Trp$^2$-β-lipotropin fragment 61–87 amide is prepared from the protected peptide resin of Example 45 by the method of Example 2.

EXAMPLE 47

O-Benzyl-D-Ser$^2$-protected β-lipotropin fragment 61–87 benzhydrylamine resin is prepared by the method of Example 33 using t-Boc-O-benzyl-D-serine in place of t-Boc D-alanine.

EXAMPLE 48

D-Ser$^2$-β-lipotropin fragment 61–87 amide is prepared from the protected peptide resin of Example 47 by the method of Example 2.

EXAMPLE 49

O-Benzyl-D-Thr$^2$-protected β-lipotropin fragment 61–87 benzhydrylamine resin is prepared by the method of Example 33, using t-Boc-O-benzyl-D-threonine in place of t-Boc-D-alanine.

EXAMPLE 50

D-Thr$^2$-β-lipotropin fragment 61–87 amide is prepared from the protected peptide resin of Example 49 by the method of Example 2.

EXAMPLE 51

D-Met$^2$-protected β-lipotropin fragment 61–87 benzhydrylamine resin is prepared by the method of Example 33 using t-Boc D-methionine in place of t-Boc D-alanine.

EXAMPLE 52

D-Met$^2$-β-lipotropin fragment 61–87 amide is prepared from the protected peptide resin of Example 51 by the method of Example 2.

EXAMPLE 53

D-Glu$^2$-protected β-lipotropin fragment 61–87 benzhydrylamine resin is prepared by the method of Example 33 using t-Boc-gamma benzyl-D-glutamic acid in place of t-Boc D-alanine.

EXAMPLE 54

D-Glu$^2$-$\beta$-lipotropin fragment 61–87 amide is prepared from the protected peptide resin of Example 53 by the method of Example 2.

EXAMPLE 55

D-Gln$^2$-protected $\beta$-lipotropin fragment 61–87 benzhydrylamine resin is prepared by the method of Example 33 using t-Boc-D-glutamine in place of t-Boc D-alanine.

EXAMPLE 56

D-Gln$^2$-$\beta$-lipotropin fragment 61–87 amide is prepared from the protected peptide resin of Example 55 by the method of Example 2.

EXAMPLE 57

$\alpha$-Benzyl-D-Asp$^2$-protected $\beta$-lipotropin fragment 61–87 benzhydrylamine resin is prepared by the method of Example 33 using t-Boc $\alpha$-benzyl-D-aspartic acid in place of t-Boc D-alanine.

EXAMPLE 58

D-Asp$^2$-$\beta$-lipotropin fragment 61–87 amide is prepared from the protected peptide resin of Example 57 by the method of Example 2.

EXAMPLE 59

D-Asn$^2$-protected $\beta$-lipotropin fragment 61–87 benzhydrylamine resin is prepared by the method of Example 33 using t-Boc D-asparagine in place of t-Boc D-alanine.

EXAMPLE 60

D-Asn$^2$-$\beta$-lipotropin fragment 61–87 amide is prepared from the protected peptide resin of Example 59 by the method of Example 2.

EXAMPLE 61

N-Epsilon-2-chlorobenzyloxycarbonyl-D-Lys$^2$-protected $\beta$-lipotropin fragment 61–87 benzhydrylamine resin is prepared by the method of Example 33 using t-Boc-N-epsilon-2-chlorobenzyloxycarbonyl-D-lysine in place of t-Boc D-alanine.

EXAMPLE 62

D-Lys$^2$-$\beta$-lipotropin fragment 61–87 amide is prepared from the protected peptide resin of Example 61 by the method of Example 2.

EXAMPLE 63

N-guanidinotosyl-D-Arg$^2$-protected $\beta$-lipotropin fragment 61–87 benzhydrylamine resin is prepared by the method of Example 33, using t-Boc-N-guanidinotosyl-D-arginine in place of t-Boc D-alinine.

EXAMPLE 64

D-Arg$^2$-$\beta$-lipotropin fragment 61–87 amide is prepared from the protected peptide resin of Example 63 by the method of Example 2.

EXAMPLE 65

The methyl ester of D-Ala$^2$-$\beta$-lipotropin fragment 61–87 is prepared from the protected peptide of Example 1 by cleaving the peptide from the resin with methanol (50 ml) in the presence of triethylamine (40 ml). Removal of the protecting groups is carried out according to the method of Example 2 by treating the peptide with hydrogen fluoride.

EXAMPLE 66

The ethyl ester of D-Leu$^2$-$\beta$-lipotropin Fragment 61–87 is prepared by the method of Example 65 from the protected peptide resin of Example 3, using ethanol in place of methanol and conducting the reaction at elevated temperature.

EXAMPLE 67

The n-propyl ester of D-Ile$^2$-$\beta$-lipotropin fragment 61–87 is prepared by the method of Example 66 from the protected peptide resin of Example 5, using n-propanol instead of ethanol.

EXAMPLE 68

The iso-propyl ester of D-Val$^2$-$\beta$-lipotropin fragment 61–87 is prepared from the protected peptide resin of Example 7, by the method of Example 66, using iso-propanol in place of ethanol.

EXAMPLE 69

The n-butyl ester of D-Phe$^2$-$\beta$-lipotropin fragment 61–87 is prepared from the protected peptide resin of Example 9, by the method of Example 66, using n-butanol instead of ethanol.

EXAMPLE 70

The tert-butyl ester of D-Typ$^2$-$\beta$-lipotropin fragment 61–87 is prepared from the protected peptide resin of Example 11 by the method of Example 66, using tert-butanol instead of ethanol.

EXAMPLE 71

The sec-butyl ester of D-Trp$^2$-$\beta$-lipotropin fragment 61–87 is prepared from the protected peptide resin of Example 13 by the method of Example 66, using the sec-butanol instead of methanol.

EXAMPLE 72

The n-pentyl ester of D-Ser$^2$-$\beta$-lipotropin fragment 61–87 is prepared from the protected peptide resin of Example 15 by the method of Example 66, using n-pentanol instead of ethanol.

EXAMPLE 73

The n-hexyl ester of D-Thr$^2$-$\beta$-lipotropin fragment 61–87 is prepared from the protected peptide resin of Example 17 by the method of Example 66, using n-hexanol instead of ethanol.

EXAMPLE 74

The methyl ester of D-Met$^2$-$\beta$-lipotropin fragment 61–87 is prepared from the protected peptide resin of Example 19 by the method of Example 65.

EXAMPLE 75

The ethyl ester of D-Glu$^2$-$\beta$-lipotropin fragment 61–87 is prepared from the protected peptide resin of Example 21 by the method of Example 66, using ethanol in place of ethanol.

EXAMPLE 76

The 2-methylpentyl ester of D-Gln$^2$-$\beta$-lipotropin fragment 61–87 is prepared from the protected peptide resin of Example 23 by the method of Example 66, using 2-methypentyl alcohol in place of ethanol.

EXAMPLE 77

The 2,3-dimethylbutyl ester of D-Asp$^2$-$\beta$-lipotropin fragment 61-87 is prepared from the protected peptide resin of Example 25 by the method of Example 66, using 2,3-dimethylbutyl alcohol in place of ethanol.

EXAMPLE 78

The iso-propyl ester of D-Asn$^2$-$\beta$-lipotropin fragment 61-87 is prepared from the protected peptide resin of Example 27 by the method of Example 66, using iso-propanol in place of ethanol.

EXAMPLE 79

The n-propyl ester of D-Lys$^2$-$\beta$-lipotropin fragment 61-87 is prepared from the protected peptide resin of Example 29 by the method of Example 66, using n-propanol in place of ethanol.

EXAMPLE 80

The 2,2-dimethylpropyl ester of D-Arg$^2$-$\beta$-lipotropin fragment 61-87 is prepared from the protected peptide resin of Example 31 by the method of Example 66, using 2,2-dimethylpropanol in place of ethanol.

The following examples are illustrative of the preparation of the alkylamides and dialkylamides of this invention.

EXAMPLE 81

D-Ala$^2$-$\beta$-lipotropin fragment 61-87 methylamide is prepared by reacting the peptide resin of Example 1 with a large excess of methylamine in dimethylformamide and removal of the side-chain protecting groups of the cleaved methylamide peptide by treatment with hydrogen fluoride in the presence of anisole under the conditions described in Example 1.

EXAMPLE 82

D-Leu$^2$-$\beta$-lipotropin fragment 61-87 ethylamide is prepared from the protected peptide resin of Example 3 by the method of Example 81 using ethyl amine in place of methyl amine.

EXAMPLE 83

D-Ile$^2$-$\beta$-lipotropin fragment 61-87 n-propylamide is prepared from the protected peptide resin of Example 5 by the method of Example 81, using n-propyl amine in place of methyl amine.

EXAMPLE 84

D-Val$^2$-$\beta$-lipotropin fragment 61-87 n-butylamide is prepared by the method of Example 81 from the protected peptide resin of Example 7 using n-butyl amine in place of methyl amine.

EXAMPLE 85

D-Phe$^2$-$\beta$-lipotropin fragment 61-87 n-pentylamide is prepared by the method of Example 81 from the protected peptide resin of Example 9 using n-pentyl amine in place of methyl amine.

EXAMPLE 86

D-Tyr$^2$-$\beta$-lipotropin fragment 61-87 dimethylamide is prepared by the method of Example 81 from the protected peptide resin of Example 11, using dimethyl amine in place of methyl amine.

EXAMPLE 87

D-Trp$^2$-$\beta$-lipotropin fragment 61-87 diethylamide is prepared by the method of Example 81 from the protected peptide resin of Example 13, using diethyl amine in place of methyl amine.

EXAMPLE 88

D-Ser$^2$-$\beta$-lipotropin fragment 61-87 di-n-propyl amide is prepared by the method of Example 81 from the protected peptide resin of Example 15, using di-n-propyl amine in place of methyl amine.

EXAMPLE 89

D-Thr$^2$-$\beta$-lipotropin fragment 61-87 iso-butylamide is prepared by the method of Example 81 from the protected peptide resin of Example 17, using iso-butylamine in place of methyl amine.

EXAMPLE 90

D-Met$^2$-$\beta$-lipotropin fragment 61-87 methylamide hydrochloride is prepared by reacting the free base, prepared by the method of Example 81 from the peptide resin of Example 51, with dilute hydrochloric acid.

EXAMPLE 91

D-Glu$^2$-$\beta$-lipotropin fragment 61-87 amide oxylate is prepared by reacting the free base of Example 54 with oxalic acid.

EXAMPLE 92

D-Gln$^2$-$\beta$-lipotropin fragment 61-87 amide hydroiodide is prepared by reacting the free base of Example 56 with hydroiodic acid.

EXAMPLE 93

D-Asp$^2$-$\beta$-lipotropin fragment 61-87 amide citrate is prepared by reacting the free base of Example 58 with citric acid.

EXAMPLE 94

D-Asn$^2$-$\beta$-lipotropin fragment 61-87 amide hydrobromide is prepared by reacting the free base of Example 60 with hydrobromic acid.

EXAMPLE 95

D-Lys$^2$-$\beta$-lipotropin fragment 61-87 amide sulfate is prepared by reacting the free base of Example 62 with dilute sulfuric acid following the method of Example 91.

EXAMPLE 96

D-Arg$^2$-$\beta$-lipotropin fragment 61-87 amide laurate is prepared by reacting the free base of Example 62 with lauric acid, (mm) following the method of Example 91.

EXAMPLE 97

D-Ala$^2$-$\beta$-lipotropin fragment 61-87, sodium salt is prepared by reacting the acid of Example 2 with dilute sodium hydroxide.

It will be apparent to those skilled in the art that Examples 1-97 are illustrative and that any compound of this invention can be prepared following the methods of appropriate Example set forth herein or other known solid state peptide synthesis methods.

The present invention includes within its scope pharmaceutical compositions comprising, as an active ingredient, at least one of the compounds of Formula I in association with a pharmaceutical carrier or diluent. The compounds of this invention can be administered by oral, parenteral (intramuscular, intraperitoneal, intravenous or subcutaneous injection), nasal, vaginal, rectal or sublingual routes of administration and can be formulated in dosage forms appropriate for each route of administration.

Solid dosage forms for oral administration include capsules, tablets, pills, powders and granules. In such solid dosage forms, the active compound is admixed with at least one inert diluent such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides, such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 0.001 to 100 mg/kg. of body weight daily are administered to mammals to obtain effective relief from pain or to relieve depression.

The following examples further illustrate the pharmaceutical compositions which are a feature of this invention.

EXAMPLE 98

Tablets weighing 200 mg. and having the following compositions are formulated:

| Ingredient | Mg |
| --- | --- |
| D-Ala$^2$-$\beta$-lipotropin fragment 61–82 | 50 |
| Starch | 120 |
| Collodial silica | 27 |
| Magnesium stearate | 3 |

EXAMPLE 99

Sterile 10 ml. ampules are prepared containing 10 mg. per ml. of D-Ala$^2$-$\beta$-lipotropin fragment 61–87 ethyl ester 0.1 percent sodium bisulfate, 0.7 percent sodium chloride and 0.5 percent chlorobutanol as a preservative.

EXAMPLE 100

Topical aqueous formulations for administration by nose drops or nasal spray are formulated containing 1 mg. of D-Ile$^2$-$\beta$-lipotropin fragment 61–87 amide, 3.8 mgm. glycerine, 40 mg. sorbital, 0.02 mg. benzalkonium chloride and purified water q.s. 1 m.

EXAMPLE 101

Vaginal suppositories are prepared containing 30 mg. of D-Val$^2$-$\beta$-lipotropin fragment 61–87 with lactose in a base made from polyethylene glycol 400, polysorbate 80, polyethylene glycol 4000, glycerin and butylated hydroxytoluene buffered with lactic acid to an acid pH. The suppositories have an inert covering which dissolves promptly in the vagina. The covering is composed of gelatin, glycerin, water, methylparaben, propylparaben and coloring.

EXAMPLE 102

Rectal suppositories are prepared by admixing 10 mg. of D-Met$^2$-$\beta$-lipotropin fragments 61–87 methyl amide and 2% benzocaine in a base compounded with polysorbate 80, white beeswax and polypropylene glycol monostearate.

We claim:

1. Novel heptacosapeptides represented by the formula

H-Tyr-X-Gly-Phe-Met-Thr-Ser-Glu-Lys-Ser-Gln-
Thr-Pro-Leu-Val-Thr-Leu-Phe-Lys-Asn-Ala-Ile-
Ile-Lys-Asn-Ala-Tyr-Y wherein X is a chiral residue of a D-amino acid selected from the group consisting of D-alanine, D-leucine, D-isoleucine, D-valine, D-phenylalanine, D-tyrosine, D-tryptophan, D-serine, D-histidine, D-proline, D-threonine, D-methionine, D-glutamic acid, G-glutamine, D-aspartic acid, D-asparagine, D-lysine, and D-arginine; Y is selected from the group consisting of hydroxy, amino, loweralkylamino, diloweralkylamino and lower alkoxy; and the pharmaceutically acceptable salts thereof.

2. The heptacosapeptides of claim 1 wherein Y is hydroxy.

3. The heptacosapeptides of claim 1 wherein Y is amino.

4. The heptacosapeptides of claim 1 wherein Y is loweralkylamino.

5. The heptacosapeptides of claim 1 wherein Y is diloweralkylamino.

6. The heptacosapeptides of claim 1 wherein Y is lower alkoxy.

7. Novel heptacosapeptides represented by the formula

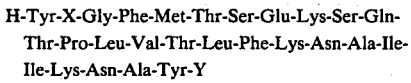

H-Tyr-X-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-Tyr-Y wherein Y is selected from the group consisting of hydroxy, amino, loweralkylamino, diloweralkylamino and lower alkoxy; and the pharmaceutically acceptable salts thereof.

8. The heptacosapeptides of claim 7 wherein Y is loweralkyalmino.

9. The heptacosapeptides of claim 7 wherein Y is diloweralkylamino.

10. The heptacosapeptides of claim 7 wherein Y is lower alkoxy.

11. D-Ala$^2$-β-lipotropin fragment 61–87 or a pharmaceutically acceptable salt thereof.

12. D-Ala$^2$-β-liptropin fragment 61–87 amide or a pharmaceutically acceptable salt thereof.

13. A pharmaceutical composition suitable for oral, parenteral, nasal, rectal or vaginal or sublingual administration comprising a therapeutically effective amount of a compound of claim 1 and a pharmaceutically acceptable carrier or diluent.

14. A pharmaceutical composition in accordance with claim 13 adapted for oral administration.

15. A pharmaceutical composition in accordance with claim 13 adapted for parenteral administration.

16. A pharmaceutical composition in accordance with claim 13 adapted for nasal administration.

17. A pharmaceutical composition in accordance with claim 13 adapted for rectal administration.

18. A pharmaceutical composition in accordance with claim 13 adapted for vaginal administration.

19. A pharmaceutical composition in accordance with claim 13 adapted for sublingual administration.

20. Novel hexadecapeptides of the formula

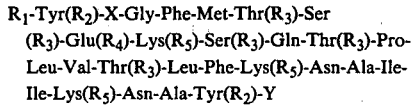

R$_1$-Tyr(R$_2$)-X-Gly-Phe-Met-Thr(R$_3$)-Ser(R$_3$)-Glu(R$_4$)-Lys(R$_5$)-Ser(R$_3$)-Gln-Thr(R$_3$)-Pro-Leu-Val-Thr(R$_3$)-Leu-Phe-Lys(R$_5$)-Asn-Ala-Ile-Ile-Lys(R$_5$)-Asn-Ala-Tyr(R$_2$)-Y wherein X' is a chiral residue of a D-amino acid selected from the group consisting of D-alanine, D-leucine, D-isoleucine, D-valine, D-phenylalanine, D-tyrosine, D-tryptophan, D-serine, D-histidine, D-proline, D-threonine, D-methionine, D-glutamic acid, D-glutamine, C-aspartic acid, D-asparagine, D-lysine and D-arginine with the limitation that when X' is D-tyrosine, D-threonine, D-serine, D-glutamine, D-lysine, D-aspartic acid or D-arginine, X' is a chiral amino acid residue protected by an R$_2$, R$_3$, R$_4$, R$_5$, R$_6$ protecting group;

R$_1$ is a N-terminus solid phase peptide synthesis protecting group selected from the group consisting of acyl-type protecting groups, aromatic urethan-type protecting groups, alkyl-type protecting groups, trialkylsilane groups, or aliphatic urethan protecting groups;

R$_2$ is a protecting group for the phenolic hydroxyl group of tyrosine selected from the group consisting of tetrahydropyranyl, tert-butyl, trityl, benzyl, 2,4-dichlorobenzyl, benzyloxycarbonyl or 2-bromobenzyloxycarbonyl;

R$_3$ is a protecting group for the alcohol hydroxy functions of serine and threonine;

R$_4$ is a protecting group for the gamma carboxyl group of glutamic acid;

R$_5$ is a protecting group for the epsilon amino group of lysine selected from the group consisting of trifluoracetyl, benzyloxycarbonyl, and 2-chlorobenzyloxycarbonyl; and R$_6$ is a protecting group for the quanidine group of arginine;

Y is selected from the group consisting of hydroxy, amino, loweralkylamino, diloweralkylamino, or lower alkoxy and a derivatized insoluble polystyrene resin support represented by the formulae

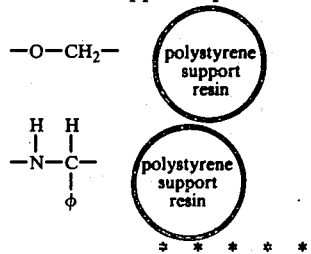

\* \* \* \* \*